United States Patent [19]

Hassler

[11] 4,218,768
[45] Aug. 19, 1980

[54] APPARATUS FOR ULTRASONIC SCANNING

[75] Inventor: Dieter Hassler, Erlangen, Fed. Rep. of Germany

[73] Assignee: Siemens Aktiengesellschaft, Berlin & Munich, Fed. Rep. of Germany

[21] Appl. No.: 850,600

[22] Filed: Nov. 11, 1977

[30] Foreign Application Priority Data

Dec. 22, 1976 [DE] Fed. Rep. of Germany ........ 2658222

[51] Int. Cl.² .............................................. G01S 9/66
[52] U.S. Cl. ..................................... 367/105; 73/612; 367/901; 367/903
[58] Field of Search .............. 340/1 R, 5 MP; 73/612, 73/614, 615, 616, 626; 367/105, 901, 903

[56] References Cited

U.S. PATENT DOCUMENTS

| | | | |
|---|---|---|---|
| 3,233,121 | 2/1966 | Chou | 307/254 |
| 3,789,350 | 1/1974 | Rolle | 340/5 MP |
| 3,815,409 | 6/1974 | Macovski | 73/615 |
| 3,881,466 | 5/1975 | Wilcox | 340/5 MP X |
| 3,895,525 | 7/1975 | Eichelberger et al. | 73/67.9 |
| 3,916,676 | 4/1975 | Boggs et al. | 73/615 |
| 3,936,791 | 2/1976 | Kossoff | 340/1 R |
| 4,012,952 | 3/1977 | Dory | 73/612 |

FOREIGN PATENT DOCUMENTS 941573 11/1963 United Kingdom .

Primary Examiner—Richard A. Farley
Attorney, Agent, or Firm—Hill, Van Santen, Steadman, Chiara & Simpson

[57] ABSTRACT

Each receiving or transmitting circuit for a respective transducer element includes an individually controllable buffer amplifier which is so operated as to avoid detrimental switching transients. For example, the buffer amplifiers in the receiving circuit may have input switches closed immediately after a transmit pulse and prior to the actual receiving phase. Then output switches of the buffer amplifiers to be activated are closed in the receiving phase, but transients so produced are blocked by the high reverse attenuation of the buffer amplifiers. The input switches may be actuated prior to activation of the transducer elements in receive mode and may serve to simultaneously supply operating voltage to the respective associated buffer amplifiers, the buffer amplifiers all being switched off during transmit mode to block transmit energy from non-active transducers. The transducers of a column of a transducer array may have their outputs summed by means of the buffer amplifiers acting as a voltage controlled current sources.

7 Claims, 6 Drawing Figures

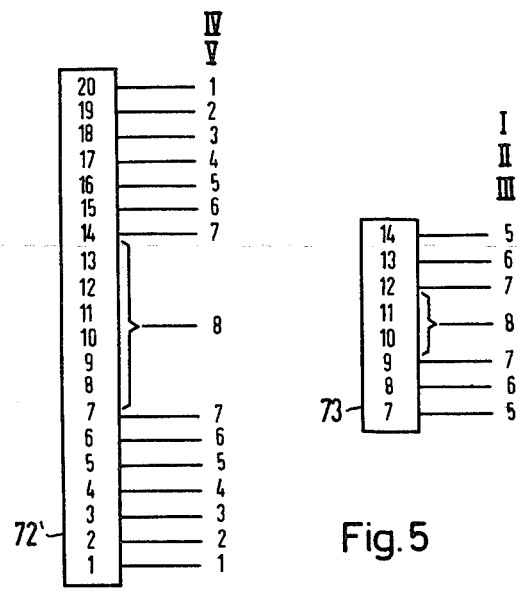
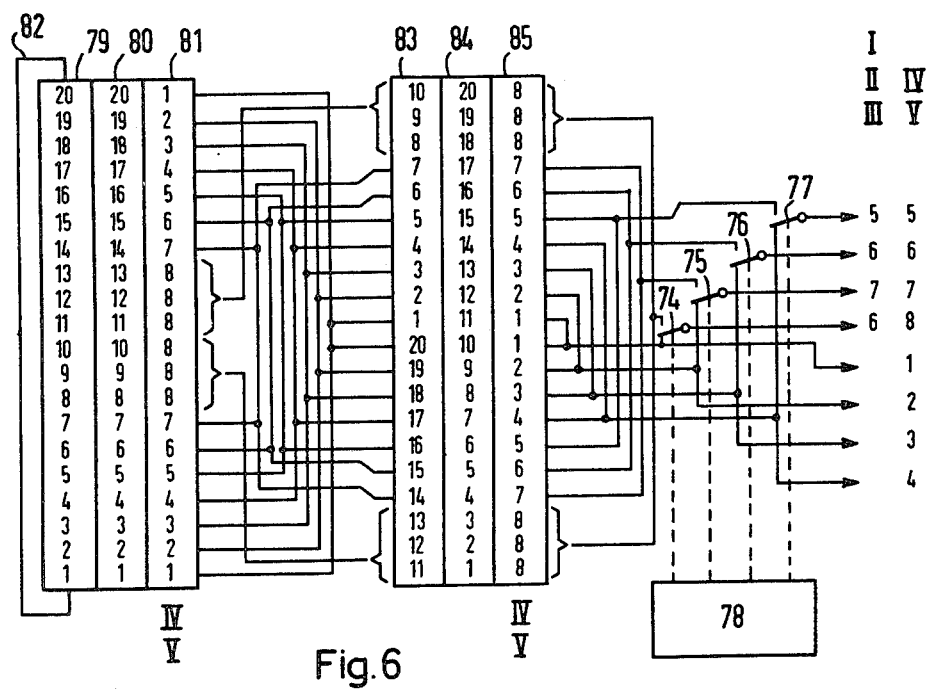

APPARATUS FOR ULTRASONIC SCANNING

CROSS REFERENCE TO RELATED APPLICATION

The present application is an improvement over applicant's copending application Ser. No. 830,173 filed Aug. 31, 1977 entitled "Apparatus For Ultrasonic Scanning", the detailed disclosure relating to the third, fourth and fifth figures of the copending application being incorporated herein as providing the background to the present improvement.

BACKGROUND OF THE INVENTION

The invention relates to an apparatus for ultrasonic scanning comprising an ultrasonic applicator consisting of a plurality of ultrasonic transducer elements spatially adjacently arranged in a surface and a control device which effects a connection of a number of ultrasonic transducers, said number corresponding to the desired focal distance, to a signal transmitter or signal receiver, respectively, in accordance with predeterminable receiving—and/or transmitting—surface patterns.

In apparatus of this type, it is necessary that switching clicks (or transients) occurring, e.g. during the connection of individual transducer elements for the purpose of producing desired receiving or also transmitting surface patterns, be attenuated to a great extent or even eliminated from the transmitting or receiving lines. Particularly in the transmit mode, in order to prepare the transmitting patterns, the switching click of the switches must lie approximately 40 dB below the transmitting voltage to be subsequently transmitted (with a given impedance of the transducer elements). Similarly, however, in the receiving mode—i.e., during the switching of the receiving surface patterns, precaution must be exercised in order that those switching interferences; i.e., switching clicks which originate from the receiving switches, also lie beneath a predetermined threshold. Practice has shown that, particularly in the latter instance; i.e., in the receiving mode, the switching clicks occurring during switching-on of the receiving patterns act like small transmitting pulses which correspondingly produce echo signals in the body tissue to be examined. However, the latter echo signals then become undesirably superimposed, in the form of echoes proximate to the skin, on the echoes emanating from greater image depths which are to be represented. In the final analysis, this leads to image falsifications (ghost images).

SUMMARY OF THE INVENTION

It is the object of the present invention to avoid the above disadvantages in the case of an apparatus of the type initially cited.

As specified by the invention, the object is achieved by virtue of the fact that at least one individual buffer amplifier for receiving and/or transmitting signals which is capable of being switched on or off, is preferably associated with each individual ultrasonic transducer element at the receiving and/or transmitting end.

A buffer amplifier for each transducer element, due to the high degree of reverse (output to input) attenuation, ensures that switching clicks occurring at the moment of the receiving and/or transmitting surface pattern switching are either incapable of reaching the respective transducer element at all or, if so, only in a very strongly attenuated fashion. The danger of an interfering effect of switching clicks on the echo image representation is thus largely eliminated by the invention.

Other important objects, features and advantages of the present invention will be apparent from the following detailed description of an illustrative embodiment, taken in connection with the accompanying sheets of drawings.

BRIEF DESCRIPTION OF THE DRAWINGS

FIGS. 5 and 6 correspond to FIGS. 5 and 6 of said referenced copending application and illustrate control programs for controlling particularly the electronic focusing so as to require the least amount of time-consumption and the least amount of circuit complexity.

DETAILED DESCRIPTION

Figure 1:
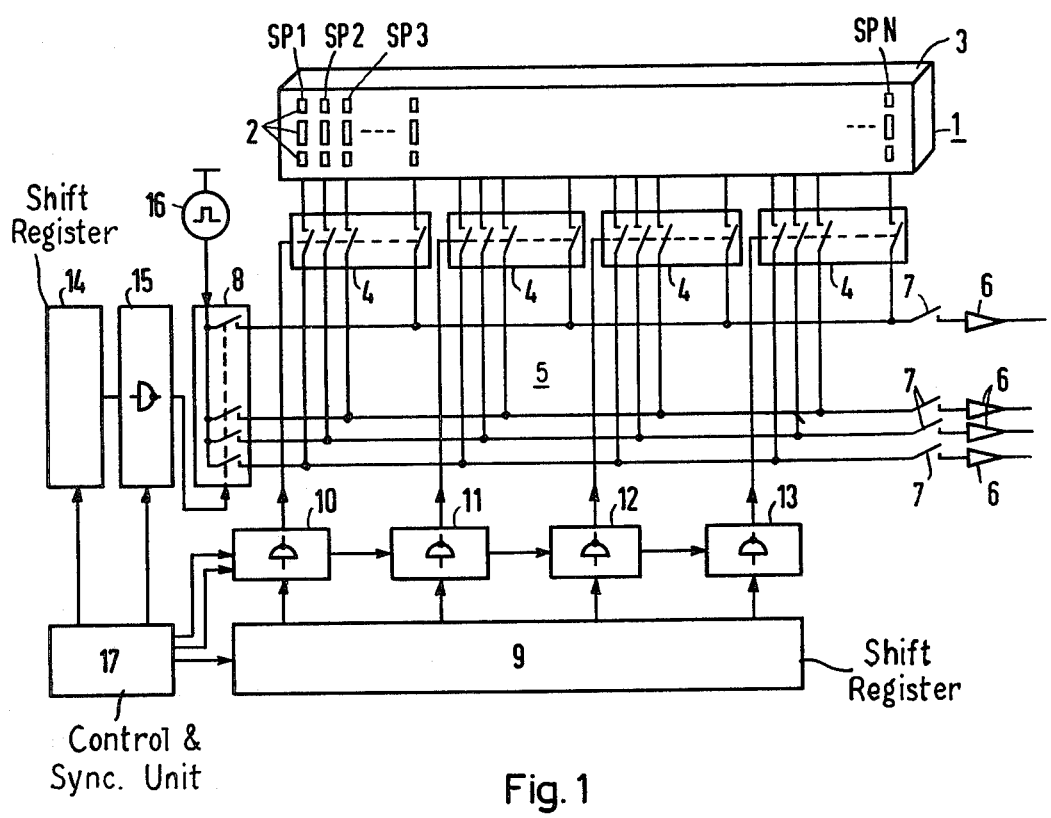
FIG. 1 illustrates the basic construction of an operating circuit of an ultrasonic array comprising a series of columns each column consisting of three ultrasonic transducer elements arranged in superimposed fashion.

In FIG. 1, the ultrasonic array is designated by reference numeral 1. It consists of a plurality of ultrasonic transducer elements 2 which are arranged in successive columns SP1, SP2, SP3, . . . SPN, on the application surface of a carrier section 3. In the present sample embodiment, the array comprises preferably 80 columns each with three superimposed transducer elements 2. The operating frequency preferably amounts to 2 MHz. Given a column width (the horizontal dimension of each column as viewed in FIG. 1) of e.g. approximately 2 mm (transducer element width plus insulating interstice) an ultrasonic image thus results which is constructed of e.g. 60 lines and has a width of approximately 12 cm (corresponding to sixty column widths, i.e. 60×2 mm) with a depth of approximately 18 cm (measured in the direction of propagation of each ultrasonic transmission pulse). With the basic scheme of FIG. 1, e.g. a total of five fixed depths of the receiving focus are to be adjustable. For this purpose, the receiving surface preferably varies between a minimum of two adjacent plates or elements of the central transducer element row on the array and a maximum of twenty transducer columns (with additional electronic focusing) consisting of all three transducer element rows. In the present applied instance, the object of the signal processing consists in reducing the data available from a total of 3×80 transducer element plates as the signal sources to e.g. a single signal in the case of purely natural focusing, or, in the case of additional electronic focusing, to initially reduce said data to eight signals and then, after a delay, also reduce these signals to one signal. Essentially a total of four functions must be satisfied here: On the one hand, the position of the effective radiator, or of the ultrasonic line to be constructed in the ultrasonic image, respectively, must be defined. On the other hand, the transmitting/receiving surface width of the effective radiator as well as its transmitting/receiving surface height must be determined. Finally, a chronologically correct switching over between transmission and reception must be guaranteed. In the basic scheme of FIG. 1, a circuit-wise reduction results by virtue of the fact that the array consisting of 3×80 individual transducer elements is through-connected in matrix fashion onto an intermediate plane consisting of a total of twenty so-called bars 5 via a total of 3×80 switching members 4, referred to in the following as surface pattern switches. Via receiving switches 7, there are connected to the end points of these bars buffer amplifiers 6 via which the signals occurring (or arriving) in the receiving mode are further conveyed for further processing. In the transmit mode, transmit switches 8 assume the distribution of the transmit signal over the individual bars 5. A first shift register 9 comprising logic blocks 10 through 13 serves the purpose of actuating the surface pattern switches 4. Actuation of transmit switches 8 proceeds by means of a second shift register 14 with the actuating (or control) logic 15. Component 16 represents the transmitting oscillator (or generator) for feeding the transducer elements 2 which are to be activated in the transmit mode. Component 17 is a control and synchronization unit for shift registers 9 and 14, respectively, and logic components 10 through 13, and 15, respectively. The functions of the above type which are to be satisfied are effected by a further breakdown of the control into operating segments. For this purpose, array 1 comprising transducer elements 2 is divided for actuation into a total of four blocks each with 20 transducer element columns. A total of 20 columns here defines the entire surface of the largest receiving surface to be adjusted in the applied instance (natural and electronic focusing). Each transducer element column of such a block then again represents the sub-unit, already cited above, consisting of three switches (e.g. S1, S11, S12 FIG. 2) of the surface pattern switches 4, which three switches are to be activated separately. The number three results from the maximum number of transducer element rows provided per array. In the sample embodiment according to FIG. 1, the eighty bit shift register 9, in addition to defining the fixedly preselected maximum surface width of the largest receiving block, also defines the position of the image line to be constructed. From left to right, twenty bits are written in block formation into shift register 9, and, for the purpose of stepping (or advancing) the image line, the twenty bit-block is advanced one bit each time in the cadence of the line rate. Logic blocks 10 through 13, connected with shift register 9, serve the purpose of determining the transmitting/receiving surface height. Depending upon the preselected program cycle, these logic blocks forward the position data supplied by shift register 9 either to all the rows of the transducer blocks or to only a portion thereof. The twenty bit shift register 14, in connection with transmit switches 8, serves the purpose of determining the respective surface width (in the horizontal direction as viewed in FIG. 1). Transmit switches 8, in dependence upon the data shift register 14, activate only as many bars 5 as correspond to the desired transmitting field width. In the receiving mode, the transmit switches 8 short-circuit all bars 5 which would result in an excessively large width of the receiving field. The buffer amplifiers 6 are temporarily cut off from the transmitting energy in the instance of transmission by the input switches 7. The illustrated operating scheme renders possible a simple and rapid programming. The height (in the vertical direction as viewed in FIG. 1) and width of the transmitting/receiving surfaces which must be changed most frequently are controlled by a very rapidly switchable logic 10 through 13, or by a very short shift register 14, respectively. Logic 15 between the short shift register 14 and transmit switches 8 permits a reprogramming or new programming of shift register 14 without interference problems such as would result from immediate corresponding actuation of transmit switches 8. In addition, the formation of an intermediate plane consisting of twenty connecting bars 5 also has the advantage that the problem of loading a single channel due to the unavoidable capacitance of connected switches in the opened state is reduced.

Figure 2:
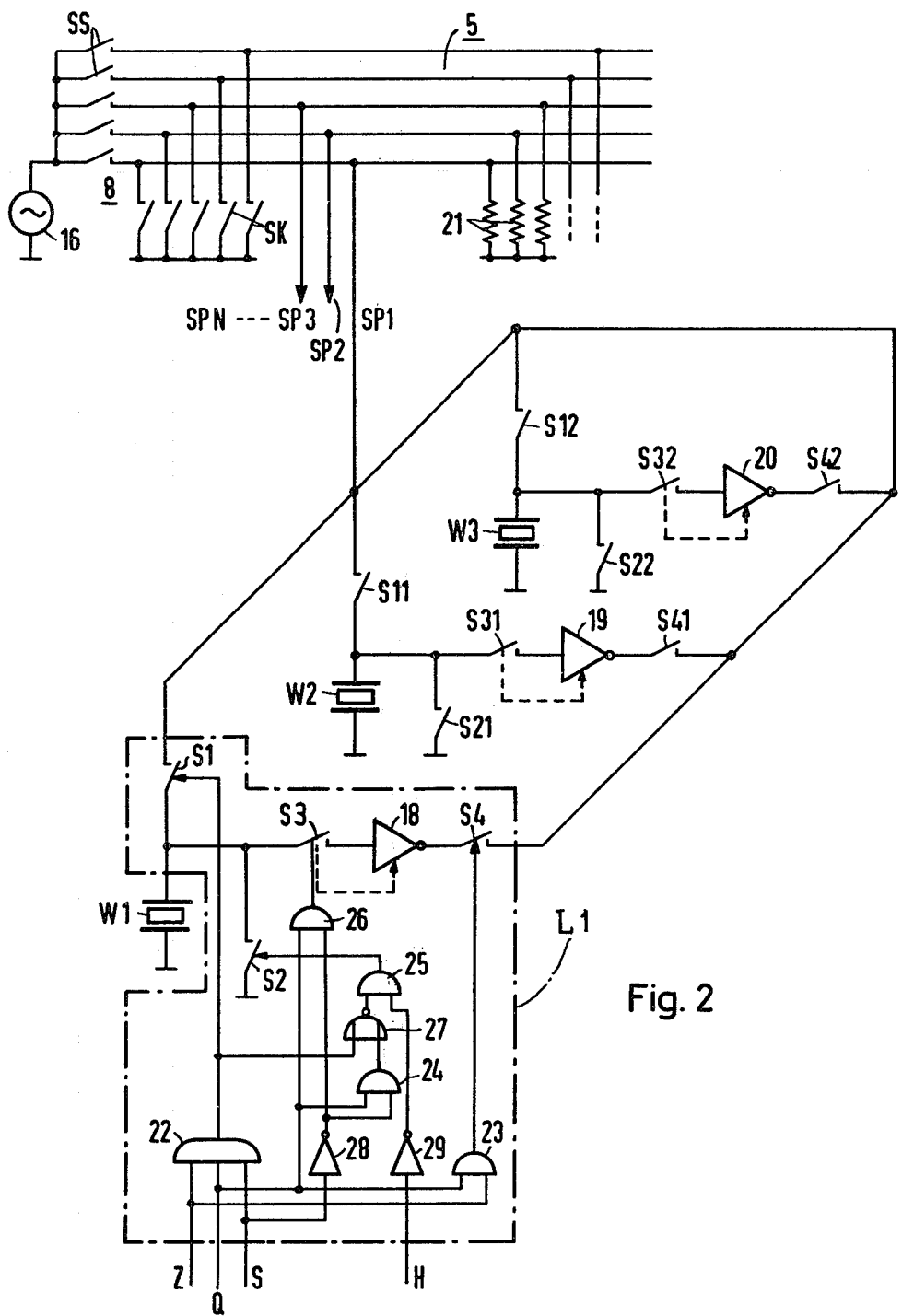
FIG. 2 illustrates the basic circuit diagram of the operating arrangement for three transducer elements, respectively, of a single column with associated buffer amplifiers for receiving operation.

A switching control device comprising buffer amplifiers, such as is sectionally illustrated in FIG. 2 for a total of three transducer elements W1, W2, and W3, of a transducer column of the ultrasonic array, serves the purpose of activating the individual transducer elements in such a manner as to avoid switching clicks (or transients). In the present case, column SP1 (FIG. 1) is illustrated, for example. The illustrated circuit and control elements correspondingly apply to all additional columns SP2, SP3, through SPN of the ultrasonic array. In the lower part of FIG. 2, the logic actuating circuit for the actuating switches of a transducer element is additionally illustrated specifically only for one single transducer element; in the present instance, transducer element W1. A corresponding actuating logic is, however, of course also provided in parallel form for additional transducer elements W2, W3, etc. In the upper part of FIG. 2, there is again illustrated part of the bar matrix 5 with transmitting generator 16 at the input of the bar matrix. Transmit switches 8 are individually constructed in the form of a combination consisting of series switches SS and short-circuit switches SK. The taps of the bar matrix 5 for the individual columns are, in turn, designated with SP1, leading to the first column of transducer elements, and SP2, SP3, by way of example, there being four taps on each of twenty bars, designated to correspond to respective columns SP1, SP2, SP3 . . . SPN, FIG. 1. As already stated, transducer elements W1, W2, and W3, are specifically associated with column SP1. In addition, there is associated with each transducer element W1, W2, or W3, a pair of switches for the purpose of actuating with transmitting energy, or tapping the receiving energy, said pair of switches consisting of a series switch and a parallel switch, similar to the transmit switches 8 of transmitting generator 16. In the case of transducer element W1, these switches are illustrated by S1 and S2, respectively; in the case of transducer element W2, by S11 and S21, respectively; and in the case of transducer element W3, by S12, and S22, respectively. In addition, in accordance with the invention, there is associated with each transducer element W1, W2, and W3, respectively, a buffer amplifier 18, 19, and 20, respectively. As illustrated, buffer amplifiers 18 through 20 have input switches S3, S31, and S32, respectively as well as output switches S4, S41 and S42, respectively. The actuating logic correspondingly comprises AND-members 22 through 26 in addition to a NOR-member 27 as well as inverting members 28 and 29. The signals arriving from the shift register 9 are conveyed to the actuating logic via inputs Z, Q, S, and H.

The mode of operation of the array-actuation logic will be apparent with the sample embodiment of FIGS. 1 and 2 as follows. In the transmit mode, depending upon how many of the transducer elements W1, W2, and W3, are to contribute to the transmitting surface pattern, correspondingly associated transmitting series switches SS are closed together with series switches S1, S11, and S12, respectively, of the transducer elements W1 through W3. The associated transmitting short-circuit switches SK and the transducer short-circuit switches S2, S21, S22, are then correspondingly opened in the case of an activated transducer element W1 through W3. Non-activated transducer elements; for example, those of the group W1 through W3 or transducer elements of other groups from the following columns SP2 through SPN, however, have respectively opened transmit switches SS, or transducer series switches, respectively, whereas the associated short-circuit switches can be closed. Upon termination of the transmitting phase; i.e., subsequent to emission of an ultrasonic impulse, there is a preparatory switching-on to reception (preferably the largest receiving surface pattern to be adjusted). For this purpose, all series switches and short-circuit switches of a transducer element are opened and transducer elements selected for specified receiving surface patterns are, in a preparatory fashion, switched to the following reception (or receive mode) through closing of the input switches of the buffer amplifiers. In the illustration of FIG. 2, this means e.g. that, in the case of a receiving surface pattern with all transducer elements W1 through W3, series switches S1, S11, and S12, respectively, are all opened, and short circuit switches S2, S21, and S22 are also opened, whereas, in contrast thereto, input switches S3, S31, S32 of buffer amplifiers 18, 19, or 20, are closed. Switching clicks (or transients) are indeed produced with the closing of these switches which, however, cannot have an interfering effect because the preliminary switching-on of the buffer amplifiers to reception proceeds outside the actual receiving phases. A switching-on to actual reception of the individual desired actual receiving surface patterns then takes place only in the receiving phase by closing the respective output switches S4, S41, and S42, of buffer amplifiers 18 through 20. In so doing, switching clicks (or transients) are indeed actually also produced in the receiving phase. However, these switching clicks (or transients) likewise cannot have an interfering effect, since, due to the high reverse attenuation of buffer amplifiers 18, 19, and 20, respectively, on the one hand, and the high degree of stop band attenuation of the transducer series switches S1, S11, and S12, respectively, in connection with the transducer impedance, on the other hand, (30 dB), these switching clicks (or transients) are unable to reach the transducer elements W1, W2, and W3, respectively, which are switched to reception. Hence, none of these transducer elements is subjected to the energy of this switching click (or transient), and thus no interfering transmit pulses result outside the desired transmitting phases.

In the sample embodiment particularly of FIG. 2, buffer amplifiers 18, 19, 20, respectively, (in a corresponding fashion, also all other buffer amplifiers of columns SP2 through SPN) operate at the output side into respective common impedances 21 at the signal outputs of the bars of the bar matrix 5, which impedances can be the input resistances of buffer amplifiers 6, in accordance with the embodiment of FIG. 1. However, instead of the buffer amplifiers, it is also possible to use oscillatory (or resonant) circuits or pure capacitances as the output impedances. As explained, when there are different receiving depths, receiving surface patterns of different size occur with correspondingly different antenna gains. Normally this leads to differences in the image brightness. Uniform brightness is achieved by providing a compensating amplifier for the echo summation signal which amplifier is preferably additionally switched over into the image blanking interval behind a depth compensation amplifier which is connected to the outlet side of the buffer amplifiers of bar matrix 5. In addition, it is worthy of note that input switches S3, S31, S32, etc., of buffer amplifiers 18, 19, 20, etc., are simultaneously switches for connecting or disconnecting the current supply of the buffer amplifiers. The buffer amplifiers 18, 19, 20, etc. may each operate as a voltage-controlled current source.

The prior copending application Ser. No. 830,173 filed Aug. 31, 1977 gives a detailed explanation of the operation of circuitry such as shown in FIG. 1, and this description is incorporated herein for the sake of further detailed explanation of this circuitry and its operation in natural and/or electronic focusing systems. Referring to the exemplary sequence of operation given in the aforementioned copending application, the operation of FIGS. 1 and 2 hereof would be as follows:

(1) For a 3×10 transmit surface, the ten switches SS corresponding to columns SP6 through SP15 are closed. (Only lines associated with columns SP1, SP2, and SP3 are actually shown in FIG. 2.) For the circuits associated with columns SP6–SP15, switches S1, S11 and S12 would be closed. The input Q, FIG. 2, can be from a stage of shift register 9, and each of the circuits of FIG. 2 associated with columns SP1–SP20 would initially have the line Q active (in a logical one condition). Where all three rows are to be activated, the individual Z input for each logic such as L1, FIG. 2, would be at logical one level prior to the transmit pulse. The individual S input to each logic segment such as L1, FIG. 2, would also be at logical one level in preparation for the transmit operation.

(2) The transmit pulse from source 16 would then be conducted via switches SS associated with columns SP6–SP15, and via series switches such as S1, S11 and S12 to the respective transducers such as W1, W2 and W3.

(3) After the transmit pulse, the Z inputs would return to zero opening the series switches such as S1, S11 and S12, and also opening the buffer amplifier output switches such as S4, S41 and S42. The input corresponding to input S, FIG. 2, for controlling switch S31 would shift to a logical zero state, providing a logical one output level from the inverter corresponding to inverter 28, FIG. 2, for the circuits associated with the middle row of transducers such as transducer W2. The short circuit switches such as S21 for the transducer elements such as W2 which are to be active in the receiving phase are switched to open condition by supplying a logical zero signal to the input corresponding to S for the middle row of transducers. At this time switches S2 and S22, for example, may be closed since the upper and lower rows of transducers (such as transducer W3 and transducer W1) are to be inactive in the initial receiving phase (phase II); for example, if input S for the lower row of transducers such as W1 is at a logical one state, the output of inverter 28 will be at a logical zero state, and the corresponding short circuit switch S2 will be closed if input H is at logical zero. At this time buffer amplifiers such as 19 have their input switches such as S31 closed, and this may produce a transient communicating with the associated transducer W2. The result is not detrimental, however, because any resultant pulse from the transducer W2 impinges on the interface with the bodily tissue during an inactive phase (phase I) and prior to receiving mode (phase II).

(4) In the receiving phase (phase II) the desired signal conducting receiving circuits are activated by closing the output switches of the buffer amplifiers to be activated, such as output switch S41, by supplying a logical one signal level to the Z input controlling the associated row of buffer amplifiers. The switching transients due to the closure of these output switches such as S41 do not reach the transducer elements such as W2, because of the high reverse attenuation of the buffer amplifiers such as 19, and the high attenuation provided by the open switches such as S1, S11 and S12.

The other operations in steps (1) through (4) are as given in the copending application, and the operation of the inputs Z, Q, S and H for the further steps (5) through (14) of the copending application will be apparent from the foregoing example, the operation of unit 17 to provide the desired Z, S and H signals being routine in this art.

With respect to the method of operation, the present application thus teaches that individual selectively connectable and/or selectively energizable buffer amplifiers may be connected between the transmitting pulse generator 16 and the respective transducers (for providing transmitting signal circuits, not shown), or between the respective transducers and the further receiver processing circuitry such as 6, 7 in FIG. 1, or 21, FIG. 2 (a common summing amplifier such as designated by reference numeral six in the first figure of the copending application optionally being associated with input impedances such as 21 if desired), in each case the buffer amplifier input switches such as S3 being closed well prior to the receiving phase, and the output switches such as S4 being closed only simultaneously with the occurrence of the respective transmit or receive phase; for the case of the receive mode, the high reverse attenuation of the buffer amplifiers isolating transients (due to actuation of the output switches) from the respective transducers.

It will be apparent that many modifications and variations may be effected without departing from the scope of the novel concepts and teachings of the present invention.

Description of FIGS. 1 and 3-6 From the Referenced Copending Application Ser. No. 830,173

Figure 4:
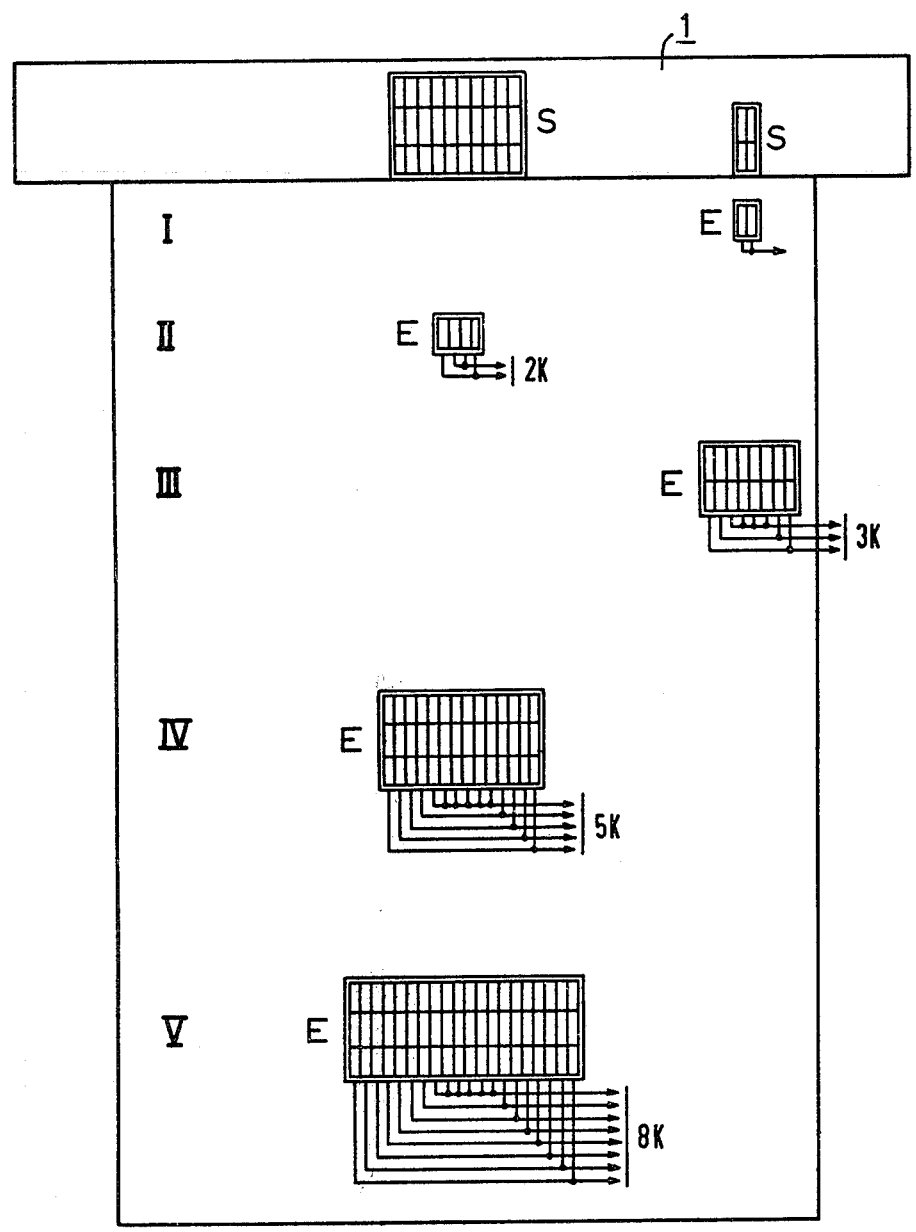
FIG. 4 corresponds to FIG. 4 of said referenced copending application and illustrates the possible image construction by means of ultrasonic arrays with blanking intervals in the case of a concomitant natural focus and with an additional focusing.

FIG. 1 of the present application corresponds with the first figure of the referenced copending application Ser. No. 830,173 except for the showing with respect to the individual amplifiers 6 and switches 7 herein. Accordingly, the description of the first figure of Ser. No. 830,173 is applicable to FIG. 1 herein, and is reproduced as follows:

With the sample embodiment according to FIG. 1, a total of approximately five fixed depths of receiver focus are to be automatically switched into effect during a scanning sequence. The receiving surface thus as indicated in FIG. 4 automatically varies between a minimum of two adjacent plates of the central transducer element row on the array (mode I in FIG. 4) and a maximum of twenty columns (in the case of additional electronic focusing) consisting of all three transducer element rows (mode V in FIG. 4). When there is additional electronic focusing, at the most eight channels for different delay times are required. The number of channels (K) used for each mode in FIG. 4 are indicated by the numeral preceding the letter K. The aforementioned data has been selected (in using approximate formulas) such that, in the case of an electronic concomitant focus, the six decibel values (6 dB-values) of the effective sonic beam width remain constantly at approximately four millimeters (4 mm) over the entire image depth. Thus, the class of image quality of conventional mechanically-moved ultrasonic scanning systems with a high image frequency is achieved. The layer thickness of the scanning fluctuates between three and eight millimeters (3 and 8 mm). However, other values correspondingly result for other operating frequencies which also comprise differently dimensioned arrays with e.g. a greater number of columns and an accordingly greater number of lines. The image dimensions fluctuate correspondingly and, accordingly, variant fixed depths of the receiving focus with correspondingly varying transmitting/receiving surfaces result.

Figure 3:
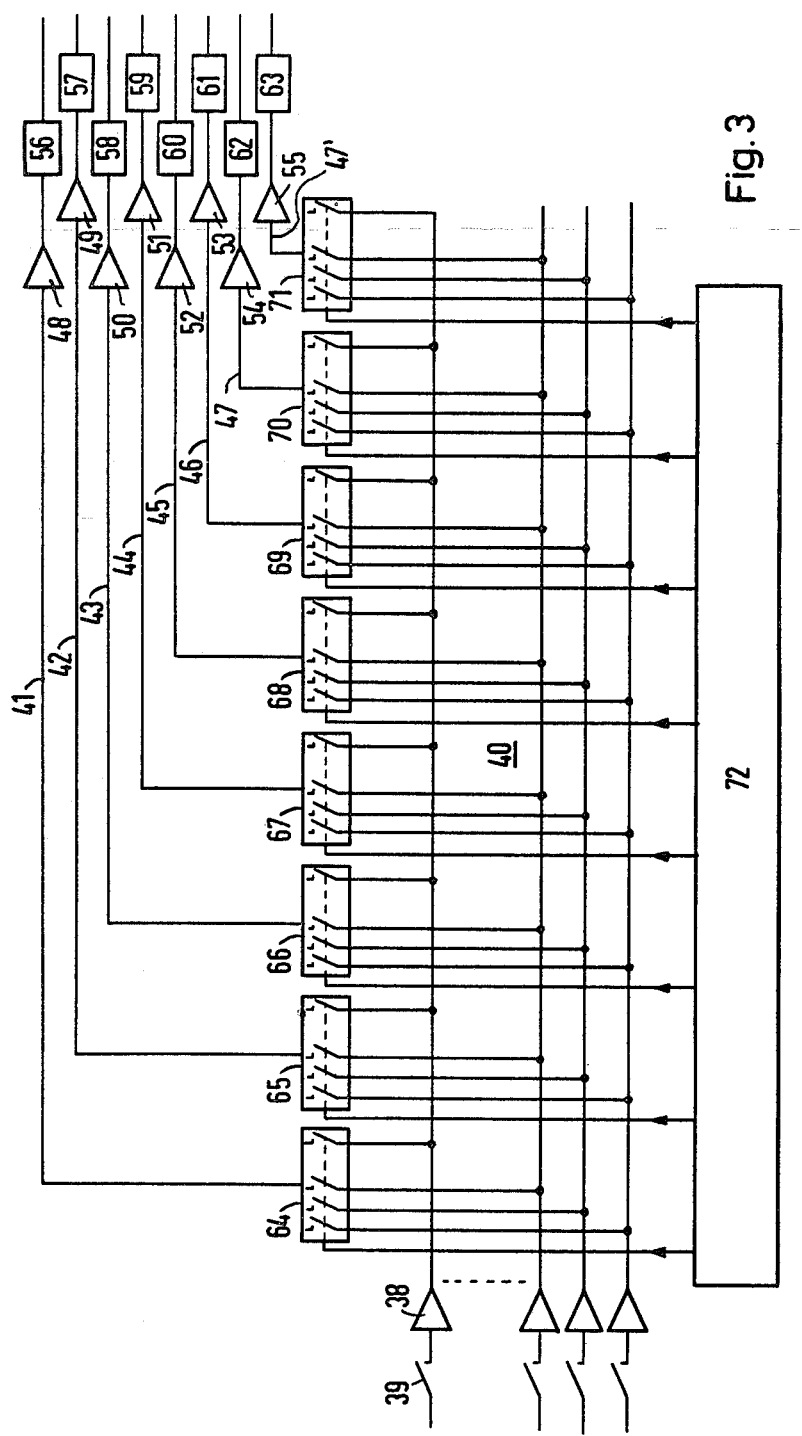
FIG. 3 corresponds to FIG. 3 of the referenced copending application Ser. No. 830,173 and illustrates a basic circuit diagram for the realization of an additional electronic focusing.

In the present applied instance, the object of the signal processing consists in reducing the data available from a total of $3 \times 80$ transducer element plates 2 (acting as signal sources) to a single signal in the case of purely natural focusing; or, in the case of additional electronic focusing (e.g. as shown in FIG. 3), to first reduce said data to eight signals and then, after a delay, to also reduce it to one signal. Essentially, there are four functions which must be satisfied here. On the one hand, the position of the effective radiator or of the ultrasonic line to be constructed in the ultrasonic image must be defined. On the other hand, the transmitting/receiving surface-width of the effective radiator as well as its transmitting/receiving surface-height must be determined. Finally, a chronologically correct switching over between transmission and reception must be guaranteed. Theoretically, it is possible to carry out a circuit reduction to one channel with a series switch per ultrasonic vibrating plate. For a direct reduction to a total of eight channels (without an intermediate stage), eight series switches for each plate 2 would be necessary; i.e., thus, $8 \times 240 = 1920$ individual switches. Regarding the latter instance, however, a less costly solution results if redundancies are avoided and at least one intermediate stage of reduction is formed. Therefore, in order to achieve a certain unit-by-unit expansibility, a total of two successive stages are selected for the signal processing, which stages can be used selectively in combination or also individually. The first expansion stage makes possible a scanning according to the principle of the concomitant natural focus; in contrast thereto, the second expansion stage makes possible an additional electronic focusing (basic circuit diagram according to FIG. 3). Both stages have been judiciously selected such that a new programming or a reprogramming of switch positions can be carried out easily and rapidly while the construction of an image line is still in progress. By creating so-called blanking intervals, interferences caused by the influence of control signals on transmitting (or receiving) channels are eliminated to a great extent, as shall be further explained in the following. Regarding the sample embodiment according to FIG. 1, the circuit-reduction results in such a manner that the array consisting of $3 \times 80$ individual transducer elements 2 is interconnected in a matrix-fashion on an intermediate plane consisting of a total of twenty so-called bus bars or matrix conductors 5, said interconnection proceeding via a total of 3×80 switching members (FIG. 2) which comprise an implementation of blocks 4, and are referred to in the following as surface pattern switches.

If, however, additional electronic focusing subsequently is selected—for example, in accordance with the basic circuit diagram of FIG. 3—all twenty bars 5 are connected separately, via one receiving switch (39, FIG. 3) and associated buffer amplifier (38, FIG. 3) each, to the following circuit. In the transmitting instance, transmit switches 8 assume the distribution of the transmit signal to the individual bars 5. In order to actuate the surface-pattern switches of blocks 4 there is a first shift register 9 with logic blocks 10 through 13. Actuation of the transmit switches 8, however, is controlled by means of a second shift register 14 with the actuating logic 15. Component 16 represents the transmitting oscillator for feeding transducer elements 2 which are to be activated in the case of transmission. Block 17 is a control-and synchronization-unit for shift registers 9 and 14, and logic blocks 10 through 13, and 15. The functions of the above type which are to be carried out require an additional break-down. For this purpose, array 1 comprising transducer elements 2 is divided for actuation into a total of four similar blocks each with twenty transducer columns. Altogether twenty columns define the entire area of the largest receiving surface (mode V, FIG. 4) to be adjusted in an applied instance (natural and electronic). Each transducer element column of such a block then again represents the previously above-described sub-unit consisting of three switches of one of the blocks of the surface pattern switches 4 which are to be actuated separately. The number three results from the maximum number of transducer element rows provided per array. In the sample embodiment according to FIG. 1, the 80-bit-shift register 9, in addition to defining the fixedly preselected maximum surface width of the largest receiving block (mode V, FIG. 4), also defines the position of the image line to be constructed. Thus, proceeding from left to right, twenty bits are recorded into shift register 9 in block formation, for example at the twenty left most register stages, and, for the purpose of stepping (or advancing) the image line, the twenty bit-block is advanced (to the right as viewed in FIG. 1) one bit each time in the clock pulse (or cadence) of the line. Logic blocks 10 through 13, which are connected to shift register 9, serve the purpose of determining the height of the transmit/receive surface. Depending upon the preselected program cycle, these logic blocks convey the position data supplied by shift register 9 either to all the rows of the transducer blocks or to only a fraction thereof. The twenty bit-shift register 14, in connection with transmit switches 8, serves the purpose of determining the respective surface width. Transmit switches 8, which are dependent upon the data of shift register 14, activate only as many bars 5 as correspond to the desired width of the transmit field. In the receiving mode, transmit switches 8 may be actuated to prevent transmission of echo signals from certain of the transducer element columns, even though such columns have been enabled by means of shift register 9 as shown in FIG. 2.

In the transmitting mode, the matrix conductors 5 are again electrically isolated so that a transmit pulse applied to one matrix conductor is not coupled to matrix conductors having an associated open switch 8. At the instant of transmission, the amplifiers 38, FIG. 3, are temporarily cut off from the transmitting energy by the input switches 39, FIG. 3.

The actuating scheme described renders possible a simple and rapid programming. The height and width of the transmit/receive surfaces which may be changed most frequently are controlled by means of a rapidly switchable logic 10 through 13, or merely by means of a short shift register 14, respectively. Logic 15 between the short shift register 14 and the transmit switches 8 thus permits a reprogramming or new-programming of the shift register 14 without interference problems which would be caused by the concurrent actuating of the transmit switches 8. The formation of an intermediate plane consisting of twenty connective bars or matrix conductors 5 has the additional advantage in that the problem of loading an individual channel with the unavoidable capacitance of connected switches in the opened state is diminished.

If an additional concomitant electronic focusing is desired, the circuit diagram according to FIG. 1 must be expanded correspondingly by that of FIG. 3. The problem existing here consists in distributing the signals of now all twenty bars of the bar-matrix 5 according to FIG. 1 over a total of eight channels with varying delay times. The total number of eight channels is the result of the requirement for as low as possible a self-(or inherent, or natural) directional effect on the part of the receiving columns with a given receiving surface width and a given focal distance. The division of the receiver width into a finite as opposed to an infinite number of columns or channels, respectively, of varying electronic delay times results in a quantization error which is not permitted to exceed a specific quantity. This quantity amounts to one-eighth of the ultrasonic wavelength, from which the minimal number of channels is also derived. In the case of preselection of only eight channels, the allocation of individual columns to the channels must be changed while the construction of an image line is still in progress. With a reduced circuit complexity, however, this necessitates a reprogramming during the line construction. However, if a total of ten channels is employed for the purpose of signal delay, the allocation of the columns to the channels can be kept constant with the program remaining the same; however, the circuit complexity is correspondingly great. Accordingly, with an additional electronic focusing, there is provided the connection of the fundamental circuit diagram according to FIG. 3 with that of FIG. 1 via a total of twenty buffer amplifiers 38 with input channel switches 39. In the arrangement illustrated in FIG. 3, each of the matrix conductors 5 of FIG. 1 is entirely electrically isolated from the other matrix conductors, and such entirely separate matrix conductors have been designated 5 (1) through 5 (20) at the left in FIG. 3. Thus, in FIG. 3, the matrix conductor 5 (1) is only connected with the twentieth switch position of each of the blocks 4 in FIG. 1 and is not connected with any of the other matrix conductors such as 5 (18), 5 (19) and 5 (20) which are actually shown at the left in FIG. 3.

Disposed at the outputs of the twenty buffer amplifiers 38, FIG. 3, there are the twenty further bus bars of a matrix 40. Each of these bars is now capable of being interconnected into a total of eight individual channels 41 through 47, 47' having a total of eight channel amplifiers 48 through 55 with outlet-connected delay members 56 through 63 providing respective different delay times. Analog switches integrated into packets 64 through 71 serve the purpose of selective connection. The position of all 20×8=160 individual switches is defined by a 160 bit-shift register 72. With the basic circuit diagram according to FIG. 3, the electronic focusing is to be laid out such that the focus lies on the axis of symmetry in front of the respective receiving surface. Accordingly, columns disposed symmetrically to this axis can be associated with the same delay channels. This symmetry requirement makes possible an additional economizing of individual channels. A control program for shift register 72, which makes possible a symmetrization of this type (in utilizing the minimum number of eight channels), shall be explained in greater detail in the following within the framework of the image construction-functional description of the basic circuit diagrams according to FIGS. 1 and 3.

In accordance with the invention, the surface patterns for transmission and reception in the case of a concomitant actual and/or electronic focusing must be connected at the amplifier input during the construction of an image line. If switching is effected in a relatively large time interval after the transmit pulse; i.e., at times which correspond to a great image depth, the transmit-time-dependent amplification of the amplification depth compensation has reached high values. In such instances, a switchover which is particularly free of interference voltage is necessary. The most aggravating interferences are cross-talk pulses arriving from the control line of the respective control switches to the receiving line. These cross-talk pulses, which, as errors of electronic switches, can be eliminated only with great difficulty, lead to two types of image errors. In the one instance, interference signals result which lead to undesired transverse lines during image representation. In the other instance, the cross-talk pulses act as small transmitting pulses triggering echo signals particularly of the structures proximate the skin, which structures, immediately after the switchover, are represented in the form of ghost images in the visual image. Basically, the cited difficulties could be avoided by seeking a circuit plan wherein switching is carried out only subsequent to a preceding amplification; i.e., only in the case of high signal levels. However, this would lead to an undesired high component outlay, because, in the case of electronic focusing, a total of thirty independent channels would then have to be constructed.

It is more advantageous to maintain the present circuit plan and avoid interferences due to cross-talk pulses of the switches by virtue of the fact that the entire ultrasonic image is to be constructed of interleaved partial images such that blanking intervals alternately result in each partial image, in which blanking intervals it is possible to carry out switching operations without the influence of interference. The presently proposed circuit—or image construction— shall be explained in greater detail with reference to FIG. 4 on the basis of two partial images. FIG. 4 illustrates the partial image interleaving during simultaneous electronic focusing with a correspondingly conceivable association of transducer element columns with individual delay channels K. The interleaving of FIG. 4, however, can basically also be used in conjunction with pure natural focusing, the only difference being that transmitting- or receiving - surfaces having a smaller surface width as compared with electronic focusing are to be used.

Viewing FIG. 4, it is apparent that the image field comprising e.g. an image width of 12 cm and image depth of 18 cm, in the case of an array 1 which is approximately 16 cm long, is subdivided into a total of five image field regions or zones 1 through V. According to FIG. 4, the first partial image is to consist only of image field zones II, IV, and V. The size of the effective receiving surface for echo signals which is to be associated with the individual receiving surfaces is also indicated in the visual display image by the number of illustrated active transducer element with the designation E for reception. The corresponding also applies to the transmit surface at the upper image edge characterized by S. Thus, e.g. for the first partial image with a transmit surface of 3×10 transducers, the maximum receiving surface (in the case of additional electronic focusing) amounts to a total 3×20 individual transducers in zone V. In zone IV, the receiving surface has been reduced to a total of 3×14 individual transducers. The smallest receiving surface in the first partial image; namely that of zone II, exhibits only a total of four remaining active transducer elements of the center transducer element row of array 1. As implied by the showing of FIG. 4, the center line of the 3×10 transmitting surface S coincides relative to array 1 with the center lines of the receiving surfaces shown directly therebelow. Thus, for a first scanning line of the first partial image, transducer element columns number six through number fifteen may be activated with the axis of symmetry between columns number ten and eleven. Similarly, during receiving mode II, transducer elements of the center row of columns nine through twelve would be activated; in receive mode IV, transducer element columns number four through seventeen would be activated; while in receive mode V, transducer element columns one through twenty would all be active. Similarly, during construction of the second partial image line by means of the transmit pulse from the 2×2 transmit surface shown to the right in FIG. 4, transducer elements of columns ten and eleven may be activated. Then, during receive mode I, these same transducer element columns are active, while during receive mode III, columns number seven through fourteen are active. Thus, as will hereafter be explained, the illustration in FIG. 4 of the center line of the 2×2 transmitting surface as widely spaced from the 3×10 transmitting surface is for clarity only, and a multiple line jump mode of partial image scanning is not being illustrated, since for example the center line of the first transmit surface of the first partial image and of the first transmit surface of the second partial image may actually coincide so that the successive lines of the first and second partial images may actually represent a single composite line within the scanning field, such composite line as displayed being composed of two raster lines on the display with a separation (if any) on the display which corresponds to not more than one-half the interval between composite scanning lines in the scanning field represented in FIG. 4.

In the first partial image, zones I and III represent blanking intervals which are utilized for the purpose of switching over the surface patterns (transmission, receiving zone II, receiving zone IV). No blanking interval is necessary at the transition between zones IV and V, because, given additional electronic focusing, it is possible here to switch into a total of eight channels immediately after amplification of the echo signals (by amplifiers 38). In FIG. 4, the second partial image consists only of two zones I and III which serve the purpose of writing (or recording) the image in the blanking intervals of the first partial image. Regarding the second partial image, zone II now represents a blanking interval. The second partial image has a substantially lesser penetration depth than the first partial image, so that the image construction time required here remains small. However, the maximum obtainable image frequency drops slightly from, for example, approximately 70 Hz to 50 Hz due to the increased time requirement for the second partial image. The chronological composition of the total image from the two partial images according to FIG. 4 may proceed in different ways depending upon the choice of line structure. A first variant makes possible a simple and hence a rapid programming of the three shift registers 9, 14 or 72. A reprogramming of the long register 9 or 72 is only necessary in the rhythm (or cadence) of the slower image frequency, whereas the shifter pulse rate corresponds to the high line frequency. Only shift register 14 is rapidly reprogrammed. The cited first variant results during image recording in the pure interlaced scanning process; i.e., for example, the first partial image is first completely recorded, and subsequently, the first recorded partial image is supplemented by the second partial image. However, in the case of this simple interlaced scanning process, the production of the second partial image, on account of the low image depth, raises the problem that echos e.g. emanating from a greater depth are, under certain circumstances, represented on adjacent lines on account of the sonic beam width which is greater in relation to the line spacing. If the given operating frequency is 2 MHz, these echos, in the case of normal body tissue, are namely only approximately 28 dB amplitude-weaker than echos of the structure proximate the skin which is to be represented. In order to ensure that images of deeply-disposed tissue are not represented in this manner as displaced in proximity to the surface, an amplitude interval of at least 50 dB should be provided. This condition can be adhered to e.g. by increasing the operating frequency, for example, from 2 MHz to 4 MHz. However, aid can also be found in the case of a maintained 2 MHz-operating frequency by using a line jump scanning process which, in a modification, makes possible leaps (or jumps) within the individual lines, said leaps having such spatial intervals that echos emanating from a great depth are from the very start incapable of being associated with the wrong line. However, the latter possible solution requires a considerable increase in technical outlay in view of a correspondingly enlarged complexity of the programming. However, within the framework of the present invention, a second variant which avoids the line jump process is given preference. This variant consists in that respectively associated lines of the first partial image and the second partial image are produced in direct chronological succession. The interleaving of the respective lines of both partial images can proceed such that both lines are represented directly one above the other or in direct proximity adjacent one another. This type of partial image interleaving provides virtually no transition difficulties, since echos emanating from the greatest image depth are already attenuated by approximately 74 dB given the operating frequency of 2 MHz, and, during the transition in each case from one line of the second partial image to the adjacent line of the first partial image, possible interfering echos are already more strongly attenuated by approximately 34 dB than the desired echos, taking into consideration blanking zone I. However, additional refinement can be achieved by virtue of the fact that, in the case of the second partial image, operation is carried out with weaker transmit pulses, which is possible due to the lesser penetration depth of the second partial image. Thus, if the transmit pulse of the second partial image is, for example, selected to be approximately 20 dB lower than that of the first partial image, the echos are then likewise approximately 20 dB weaker. In toto, there thus results a satisfactory signal-to-noise ratio of approximately 54 dB in the case of the proposed operating frequency of 2 MHz. The conditions become yet more favorable if the operating frequency is correspondingly increased, because tissue attenuations are greater. The above stated signal-to-noise ratio of approximately 74 dB during transition from the first partial image to the second partial image merely represents a maximum value. Obviously, the drop in the power level in the case of the second partial image must be compensated by a corresponding greater amplification. However, as a consequence, the signal-to-noise ratio for the transition from the first partial image to the second partial image again drops from 74 dB to approximately 54 dB. Thus, comparable conditions regarding the signal-to-noise ratios result in the case of both image transitions.

Image construction with an additional concomitant electronic focus proceeds in partial steps on the basis of FIGS. 1 through 4 as follows:

(1) Twenty bits are inserted into the first twenty register stages (e.g. at the extreme left) of shift register 9, whereby the position of image line number one is defined. In the case of shift register 14, ten bits are placed in the center of the register. Shift register 72 is programmed once in accordance with the requirements of the symmetry axis of the sonic field.

(2) The transmit pulse follows.

(3) At some time during the construction of the first line of the first partial image; for example, during the time corresponding to image zone I of the first scanning operation, shift register 14 receives two bits in register center. Via logic 15, the transmit switches 8 are adjusted such that all the bars of the bar-matrix 5 are open; i.e., not short-circuited.

(4) Reception now takes place in zone II. The definition of the receiving width proceeds by means of selection of the channels (switching after amplification).

(5) Regarding shift register 9, the connection of the two outer transducer rows in image zone III proceeds via logic 10 through 13.

(6) Reception of zone IV takes place pursuant to a corresponding selection of the channels.

(7) Reception of zone V.

(8) A release of the register data of shift register 14 takes place via logic 15 for the purpose of adjusting the transmit switches 8, by means of the register data introduced per step (3), to the reduced transmitting surface of the first line of the following second partial image.

(9) Subsequently transmission takes place with approximately 1/10 of the previous transmit pulse amplitude.

(10) Reception now takes place in zone I, whereby the signal amplification has been increased by a factor of 10 as compared with previously.

(11) With the receiving adjustment (or setting) in zone II, shift register 14 receives ten bits for the following line position. Logic 15 here prevents the forwarding (or transfer) of the new data to the transmit switches 8.

(12) Reception of image zone III takes place pursuant to a corresponding selection of the channels.

(13) The register contents of shift register 9 is advanced by one clock pulse (1 bit) in the entire block. The corresponding occurs with the register contents of shift register 72. Regarding shift register 14, adjustment (or setting) of the transmit switches 8 proceeds in accordance with the new register contents adjusted (or set) with step (11) above.

(14) Continuation in this manner proceeds until the last image line has been scanned.

The intended simplification in the image construction results in an increased complexity of necessary program changes in the shift register. In particular, the long shift register 72 must also be reprogrammed with line frequency. However, this problem can be solved in a simple manner with distinct means. By way of example, one possible solution consists in that, in order to more rapidly reprogram shift register 72, the feeding of the shift register proceeds in a parallel operation via a plurality of feed lines. A second possibility consists in a particular arrangement of the register locations in conjunction with a change in the allocation of the channels and the delay lines (or paths). An advancement of the recorded register contents by ten pulse steps is then sufficient for the purpose of reprogramming. The third possibility, wherein it is possible to dispense entirely with reprogramming, consists, as previously indicated, in an increase in the number of channels from a total of 8, to 10, taking into account a corresponding increase in the technical outlay. Of all the possibilities indicated, possibility two is of particular interest with regard to minimizing the cost of the switching structure and programming. If, for reasons of reducing technical outlay, only eight channels are selected instead of e.g. ten channels, the allocation of the array columns to the individual channels during construction of an image line must be changed. The most favorable selection possibility of a corresponding allocation of transducer element columns to channels is apparent from FIG. 5. Accordingly, only two allocations are necessary, the one of which having to be adjusted in the image zones IV and V, whereas the other must be adjusted in the zones I, II, III. The corresponding allocation is determined by the program contents of shift register 72. In FIG. 5, the digits inside the blocks 72' or 73, respectively, each designate numbers of transducer element columns. The digits to the right of the blocks represent the respective associated channel allocations in the zones IV or V, respectively, with regard to the transducer columns of block 72', and the respective associated channel allocations of zones I, II or III, with regard to the transducer columns of block 73. In the case of shift register 72, the simplest possibility of reprogramming would consist in occupying the entire shift register comprising 160 locations (or places) with new data in each particular instance. In the case of a clock pulse frequency of 2.5 MHz, which is a sensible maximum for MOS circuits, this would still take up $0.4 \times 160 = 64$ μsec (corresponding to barely 5 cm penetration depth), so that the image frequency would have to be correspondingly reduced. Only ten steps suffice (corresponding to 4 μsec) if shift register 72 is fed back (or coupled back) into itself at intervals of twenty register locations, respectively, and if four additional analog switches are provided. FIG. 6 illustrates the latter possibility in a field of a total of twenty array-columns. The additional analog switches are referenced with numerals 74 through 77; the respective control logic is referenced with 78. In the right hand block illustration of 79 through 81, the allocation of the array-columns to the channels is shown, as these allocations are required for image zones IV and V. The digits of the blocks 79 and 80, in turn, denote the numbers of register locations, and the numbers of allocated transducer columns. The digits of block 81, in contrast thereto, denote the numbers of corresponding allocated channels of the zones IV or V, respectively. Reference numeral 82 designates the previously cited feedback line of shift register 72. In the shift register, the [consecutive] sequence of the data bits is fundamentally maintained, so that a fixed allocation between the shift register places and the channels remains. However, if, after twenty bits in each particular instance, the shift register is finally fed back (or back-coupled) and the register contents are correspondingly advanced ten clock pulses, the [respective] allocation of array-columns and channels results as illustrated in blocks 83 through 85 to the right. The similarity with the desired (or target) configurations (for image zones I, II, III) is immediately apparent. However, a transposition (or interchange) of channels as compared with the desired allocation is still present. Given a suitable programming of the delay times, this problem could be regarded as solved. However, this requires a relatively large adjustment range of the delay lines. The additional channel changeover switches 74 through 77 of channels 5, 6, 7, or 8, respectively, make possible the correct allocation in the zones I, II, and III, with a relatively narrow adjustment range of the delay line. The correct channel allocations in the different zones I through V are specifically indicated at the output of the programming circuit diagram according to FIG. 6 through specification of the corresponding channel digits or numbers. In order to simplify the illustration, a more detailed explanation of the parallel displacement of the line (or horizontal) scanning has been omitted. On the whole, the latter operation is additively superimposed on the present actuating (or control) operations. In order to avoid switch-interference problems, it would also be advantageous to arrange the analog switches 74 through 77 behind non-illustrated channel amplifiers. This makes switching at a high level possible. Only then do the switchable (programmable) delay times ensue. With the simplified reprogramming of shift register 72 corresponding to the plan of FIG. 6, a modification in the time plan of the image construction results only in the following intermediate steps. Between the above-cited switching steps (5) and (6) there is inserted a switching step (5'), during which shift register 72, in the fed-back (or back-coupled) state, is advanced ten bits at a time. In addition, the channel-changeover switches 74 through 77 are also switched over in this switching step. An additional intermediate switching step results at the end of the preceding switching step (7). In this additional switching step (7'), shift register 72 is again advanced an additional ten bits. The construction of the second partial image is thus delayed by four microseconds (4 μsec). In addition, a repeated switch-over of channel-changeover switches 74 through 77 takes place. Regarding present step (12)—i.e., reception in image zone III, however, no additional intermediate step (or a corresponding image delay) is necessary, because the channel allocation adjusted (or set) by means of shift register 72 is also required for zone II of the next partial image.

I claim as my invention:

1. Ultrasonic scanning apparatus operable for emission of an ultrasonic transmission pulse and operable during a reception phase for receiving echo pulses from varying scanning depths, during each scanning operation, said apparatus having an ultrasonic applicator comprising a plurality of ultrasonic transducer elements spatially adjacently arranged in a surface, reception means for association with the transducer elements, and control means controlling focussing of the transducer elements to varying scanning depths by connecting respective corresponding sets of said transducer elements with said reception means in accordance with predeterminable surface patterns, characterized by the following relationships which prevent switching clicks occurring in the reception phase upon switching of surface patterns from reaching the ultrasonic transducer elements as noise echoes:

(a) said reception means comprising reception lines connecting with the respective ultrasonic transducer elements; and said reception means having a series connection of a buffer amplifier (18, 19, 20, etc.), an input switch (S3, S31, S32) and an output switch (S4, S41, S42) inserted at least in the reception line of each transducer element (W1, W2, W3, etc.);

(b) each buffer amplifier (18, 19, 20, etc.) being arranged in such manner that its input is connected to the input switch (S3, S31, S32) at the transducer element (W1, W2, W3, etc.);

(c) said control means comprising a control installation for the input and output switch of each buffer amplifier which closes the input switch (S3, S31, S32) of the buffer amplifier in the time between emission of a transmission pulse and reception of echo pulses and only subsequently also closes the output switch (S4, S41, S42) for the actual reception of echo pulses, (d) said control installation providing means whereby the switching click respectively generated upon closing the input switch (S3, S31, S32) cannot disturb the transducer elements since the closing of the input switch ensues outside of the actual reception phase, and (e) said buffer amplifier providing means whereby the closing of the output switch (S4, S41, S42) in the reception phase is not disruptive because such closing only occurs at the output of the respective buffer amplifier so that switching clicks are blocked with respect to the transducer elements by means of the buffer amplifiers.

2. Apparatus according to claim 1, characterized in that during the preliminary connection of buffer amplifiers actuation of the associated input switches connects the inputs of the buffer amplifiers to respective transducer elements which are to be only subsequently activated in a receiving mode, and also connects the buffer amplifiers to a supply voltage.

3. Apparatus according to claim 2, characterized in that, with the opening of the input switch (S3, S31, S32, etc.), the buffer amplifiers are automatically switched off again from the supply voltage.

4. Apparatus according to claim 1, characterized in that the buffer amplifiers have input and output switches (S3, S31, S32, S4, S41, S42, etc.) at the input and output thereof and the ultrasonic transducer elements have series-and-short-circuit-switches (S1, S11, S12, S2, S21, S22, etc.), which are opened when the input and output switches of the buffer amplifiers are closed.

5. Apparatus according to claim 1, characterized in that respective bars of a bar matrix are connectable with respective buffer amplifiers in the receiving mode, so that the output signals of the buffer amplifiers are supplied to respective bars of the bar matrix.

6. Apparatus according to claim 1, characterized in that each buffer amplifier is preferably constructed as a voltage-controlled current source.

7. Apparatus according to claim 6, characterized in that a plurality of the buffer amplifiers, each constructed as a current source, operate at their output side into a common impedance (21) such that the signals from the respective buffer amplifiers are added at the common impedance.

* * * * *